US00PP11213P

United States Patent [19]

Guillier

[11] Patent Number: Plant 11,213

[45] Date of Patent: Feb. 8, 2000

[54] APPLE TREE NAMED 'DELKISTAR'

[75] Inventor: Gérard Guillier, Commentry, France

[73] Assignee: SociétéAnonyme des Pépiniéres et Roseraies Georges Delbard, Commentry, France

[21] Appl. No.: 09/005,577

[22] Filed: Jan. 12, 1998

[51] Int. Cl.[7] ..... A01H 5/00

[52] U.S. Cl. ..... Plt./161

[58] Field of Search ..... Plt./161

[56] References Cited

U.S. PATENT DOCUMENTS

P.P. 7,880 6/1992 Cripps ..... Plt./161

P.P. 10,669 11/1998 Lane ..... Plt./161

*Primary Examiner*—Howard J. Locker
*Assistant Examiner*—Wendy A Baker
*Attorney, Agent, or Firm*—Burns, Doane, Swecker & Mathis, L.L.P.

[57] ABSTRACT

The new apple cultivar was formed through the crossing of the 'Kidd's Orange Red' cultivar (non-patented in the United States) and the 'Bisbee Red Delicious' cultivar (U.S. Plant Pat. No. 1,565). The new cultivar displays a vigorous growth habit and is ready for harvest at mid-season. The fruit is juicy and exhibits substantial resistance to darkening when exposed to ambient conditions. The fruit is substantially asymmetric conical in configuration and is red in color (as illustrated).

4 Drawing Sheets

SUMMARY OF THE INVENTION

The new cultivar of apple tree of the present invention was created by artificial pollination wherein two parents were crossed in the hope they would contribute the desired characteristics. The female parent (i.e., the seed parent) was the 'Kidd's Orange Red' cultivar (non-patented in the United States). The male parent (i.e., the pollen parent) was the 'Bisbee Red Delicious' cultivar U.S. Plant Pat. No. 1,565). The 'Bisbee Red Delicious' cultivar is marketed under the STARKRIMSON trademark. The parentage of the new culltivar can be summarized as follows:

'Kidd's Orange Red'×'Bisbee Red Delicious'.

The seeds resulting from the above pollination were sown and 265 small plantlets were obtained which were physically and biologically different from each other. Selective study resulted in the identification of a single plant of the new variety.

It was found that the new cultivar of the present invention exhibits the following combination of characteristics:

(a) exhibits a vigorous growth habit,
(b) commonly yields an apple crop during mid-season,
(c) forms attractive large substantially asymmetric conical fruit on the tips of shoots which bears a red flush, and
(d) forms juicy fruit flesh that exhibits substantial resistance to darkening upon exposure to ambient conditions.

The new apple cultivar has been found to undergo asexual propagation and can be readily reproduced by conventional routes, such as budding (i.e., eye grafting). This asexual reproduction as performed in France has demonstrated that the characteristics of the new cultivar are strictly transmissible from one generation to another and are firmly fixed. Representative rootstocks that can be utilized with the new cultivar include the PAJAM® brand of 1 Lancep and PAJAM® brand of 2 Cepiland, M26, M9 EMLA and M9 NAKB. The particularly preferred rootstock is the PAJAM® brand of 2 Cepiland. Other rootstocks similarly can be selected taking into consideration the soil conditions and other environmental conditions that are encountered at a specific growing site.

The new cultivar of the present invention has been named 'Delkistar'.

BRIEF DESCRIPTION OF THE PHOTOGRAPHS

The accompanying photographs show typical specimens of the new cultivar as depicted in color as nearly true as it is reasonably possible to make the same in color illustrations of this character. The plant material shown in the photographs was budded on PAJAM® brand of 2 Cepiland rootstock and was grown at Malicorne, Commentry, France. A measuring stick in centimeters is included in FIGS. 1, 3, and 4 so that typical size information readily can be ascertained.

DETAILED DESCRIPTION

The following is a detailed description of the new cultivar of the present invention. The description is based upon the observation of plants when grown at Malicorne, Commentry, France while budded on PAJAM® brand of 2 Cepiland rootstock. The chart used in the identification of colors is that of The Royal Horticultural Society, London, England (R.H.S. Colour Chart). Coloration in common terms also is provided wherein such coloration is to be accorded its ordinary dictionary significance.

Tree: Semi-upright with strong vigor. In view of the strong vigor exhibited by the new cultivar, the use of a dwarf rootstock is recommended.

Figure 2:
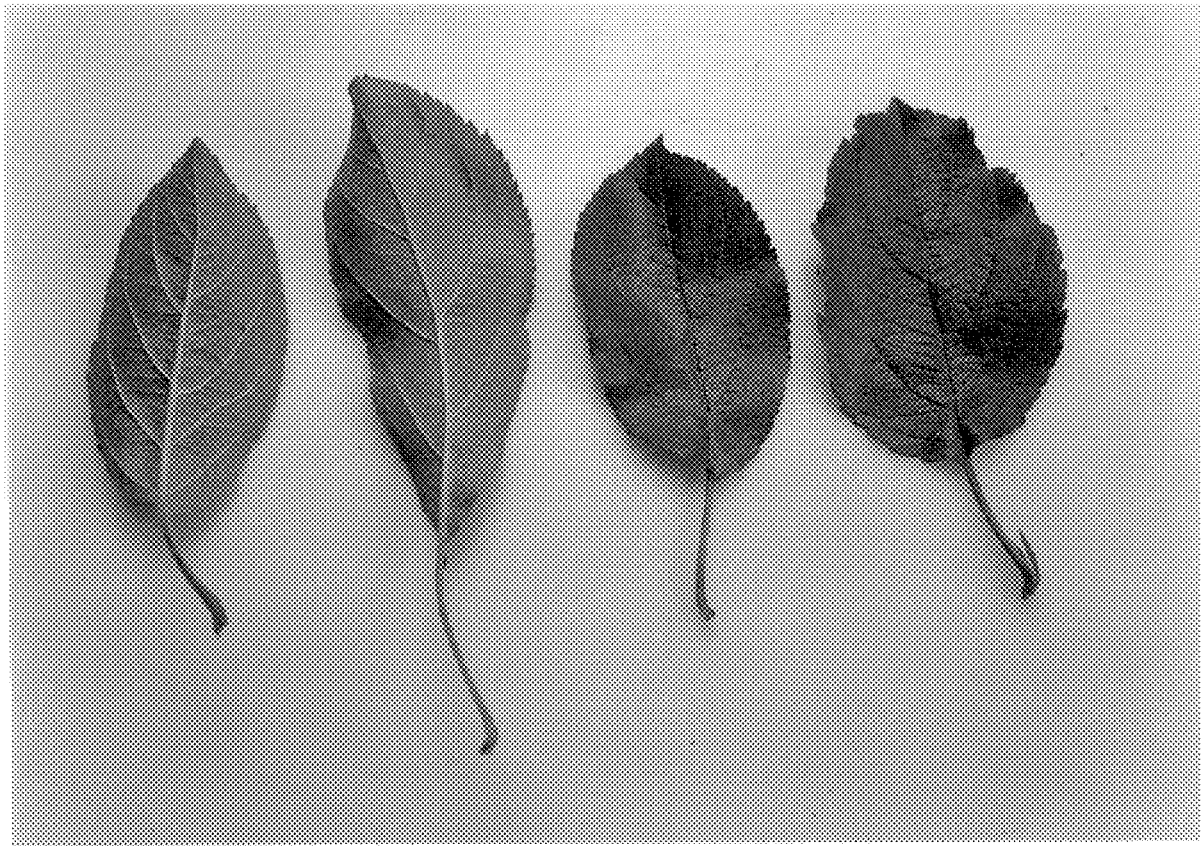
FIG. 2 illustrates typical leaves of the new variety in various stages of maturity with under surfaces being shown at the left and upper surfaces being shown at the right.

*Current season's shoots.*—Very weak pubescence, leaves extend upwards, leaves are medium in size, leaves possess medium glossiness on the upper surface and weak pubescence on the under surface, the leaf length to width ratio tends to be relatively large (see FIG. 2), and the leaf petioles tend to be long (see FIG. 2).

*Dormant one year-old shoots.*—Thick, few lenticels, and very weak pubesence.

*Bark.*—Grey-Brown Group 199A.

Leaves:

*Configuration.*—Oblong with an acuminate tip.

*Serration.*—Doubly serrate.

*Length.*—Approximately 8 cm.

*Width.*—Approximately 4.5 cm.

*Petiole.*—Approximately 3 to 3.5 cm. in length.

*Color.*—Green Group 137A on the upper surface and Green Group 138B on the under surface.

Flowers: Intermediate flowering season. The flower buds commonly burst during mid-April and bloom for approximately 15 days.

*Flower color.*—Red Group 54B.

*Flower size.*—Large, commonly when fully open approximately 4.5 cm. in diameter.

*Petal margins.*—Free.

*Petal configuration.*—Rounded.

*Petal number.*—Five.

*Fragrance.*—Slight.

Pollination requirements:

*Ploidy.*—Diploid and non-self pollinating.

*Pollinators.*—Prefer the 'Tenroy' cultivar (U.S. Plant Pat. No. 4,121).

Fruit:

*Bearing habit.*—On tips of shoots.

*Picking time.*—Medium ripening. Commonly the dates of first and last pickings are approximately the end of September and October $10^{th}$.

Figure 1:
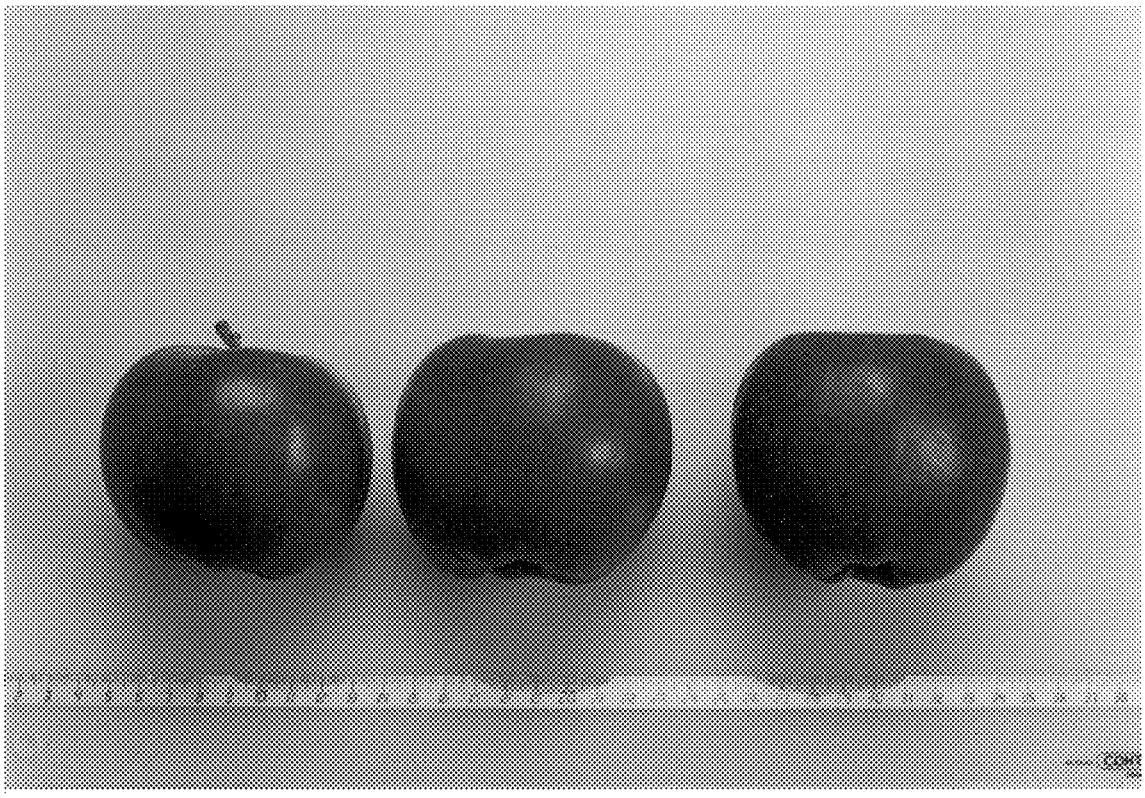
FIG. 1 illustrates typical fruit specimens of the new cultivar. The range of coloration is incluenced by the level of maturity and the position on the trees which dictates exposure to sun light.
Figure 3:
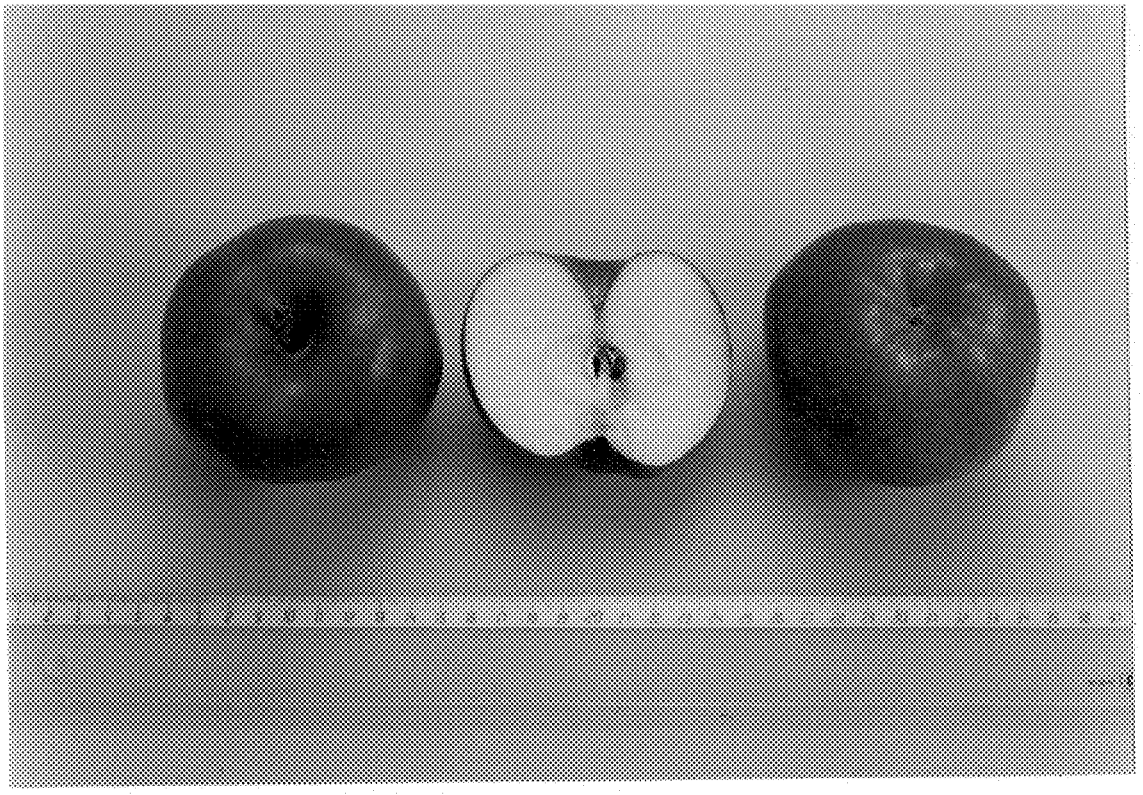
FIG. 3 illustrates typical mature fruits of the new variety from each end and in cross-section.
Figure 4:
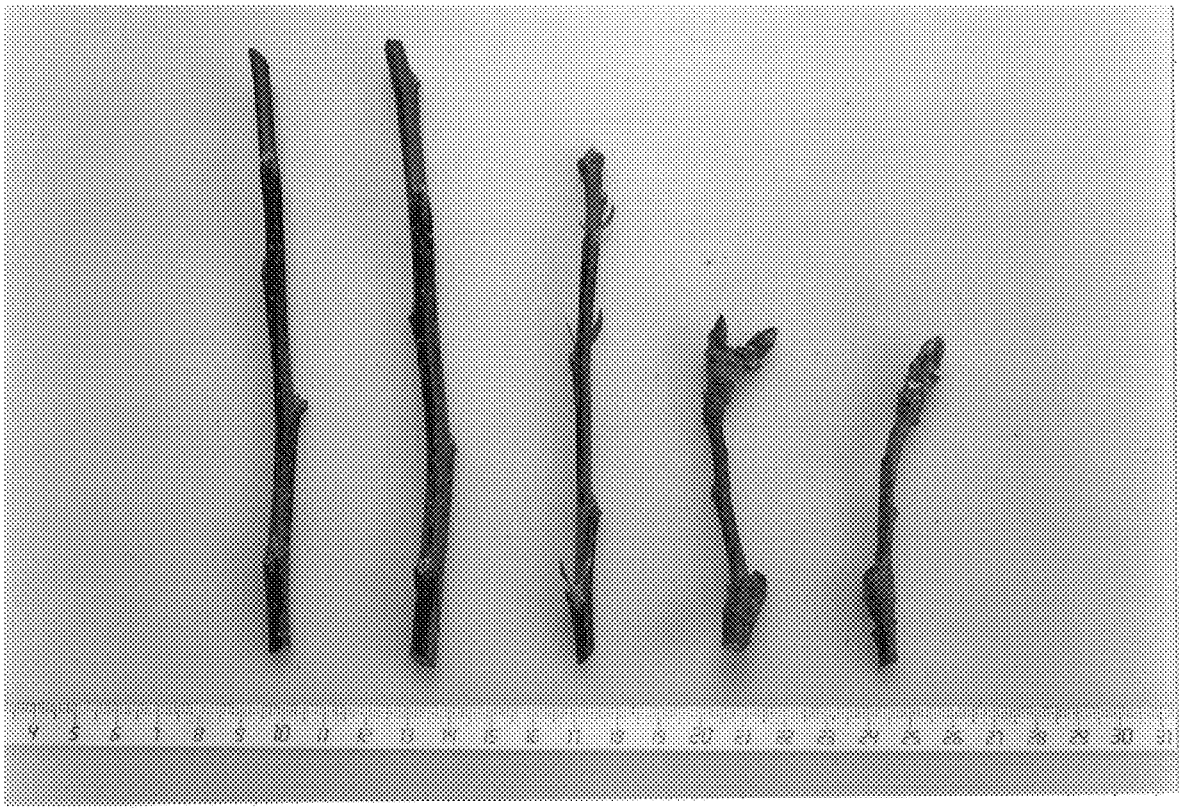
FIG. 4 illustrates typical budwood specimens of the new cultivar including dormant buds (left) and flower buds (right).

*Size.*—Large to very large (see FIGS. 1 and 3). Commonly approximately 7.2 cm. in length and approximately 7.6 cm. in width.

*Weight per apple.*—Typical apple weight ranges from approximately 220 to 250 grams.

*Form.*—Conical, commonly asymmetric, with ribbing, and strong crowning at distal end.

*Sepals.*—Long, overlapping at base.

*Eye.*—Small in size, with closed aperture, and with broad and deep basin.

*Stalk.*—Medium thickness, and medium length.

*Stalk cavity.*—Broad and deep.

*Surface relief.*—Bumpy.

*Bloom of skin.*—Absent.

*Lubricity of skin.*—Present.

*Cracking tendency of skin.*—Absent.

*Thickness of skin.*—Medium.

*Color of skin.*—Red (as illustrated), near Red Group 45C, and present as a solid flush.

*Russet.*—Present in a very low concentration primarily around the stalk cavity.

*Lenticels.*—Medium in size.

*Flesh.*—Juicy, exhibits substantial resistance to browning during the first hour after being cut, medium firmness, medium texture, yellow in coloration, near Yellow Group 13D (as illustrated in FIG. 3).

*Distinctness of core.*—Strong (see FIG. 3).

*Production.*—Very good, commonly produces harvestable fruit at an age of approximately four years. There is a slight tendency toward alternate bearing.

*Seeds.*—Near Brown Group 200D in coloration.

Resistance to diseases: Medium sensitivity to Spot and Oidium.

I claim:

1. A new and distinct cultivar of apple tree having the following combination of characteristics:

(a) exhibits a vigorous growth habit,
(b) commonly yields an apple crop during mid-season,
(c) forms attractive large substantially asymmetric conical fruit on the tips of shoots which bears a red flush, and
(d) forms juicy fruit flesh that exhibits substantial resistance to darkening upon exposure to ambient conditions;

substantially as illustrated and described.

* * * * *